(12) United States Patent
Yamaguchi et al.

(10) Patent No.: US 7,723,548 B2
(45) Date of Patent: May 25, 2010

(54) BIS(PHOSPHINE) BORONIUM SALT, PRODUCTION METHOD OF BIS(PHOSPHINE) BORONIUM SALT, AND BIS(PHOSPHINE) BORONIUM SALT PRODUCED BY THE PRODUCTION METHOD

(75) Inventors: Kentaro Yamaguchi, Sanuki (JP); Hiroshi Danjo, Sanuki (JP); Toru Koizumi, Chiba (JP); Tsuneo Imamoto, Chiba (JP)

(73) Assignee: Japan Science and Technology Agency, Chiba (JP)

( * ) Notice: Subject to any disclaimer, the term of this patent is extended or adjusted under 35 U.S.C. 154(b) by 0 days.

(21) Appl. No.: 12/067,069

(22) PCT Filed: Jan. 30, 2007

(86) PCT No.: PCT/JP2007/051431

§ 371 (c)(1),
(2), (4) Date: Mar. 17, 2008

(87) PCT Pub. No.: WO2007/091445

PCT Pub. Date: Aug. 16, 2007

(65) Prior Publication Data

US 2009/0062567 A1     Mar. 5, 2009

(30) Foreign Application Priority Data

Feb. 8, 2006     (JP)     ............... 2006-030519

(51) Int. Cl.
C07F 5/02     (2006.01)
(52) U.S. Cl. .......................................... 568/2
(58) Field of Classification Search .................. None
See application file for complete search history.

(56) References Cited

FOREIGN PATENT DOCUMENTS

JP    2002-338586 A    11/2002
JP    2004-331540 A    11/2004

OTHER PUBLICATIONS

Oohara et al., {Reactions of t-butylphosphine-borane with various electrophiles and synthesis of optically active t-butylmethylphosphine-borane, Bulletin of the Chemical Society of Japan (2002), 75(6), 1359-1365}.*

Denis et al., {B(C6F5)3-catalyzed formation of B-P bonds by dehydrocoupling of phosphine-boranes, Chemical Communications (Cambridge, United Kingdom) (2003), (1), 54-55}.*

Yamamoto et al., {Facile Synthesis of Highly Congested 1,2-Diphosphinobenzenes from Bis(phosphine)boronium Salts, Organic Letters (2006), 8(26), 6103-6106}.*

Schmidbaur al., {"Dikationen vom Hydrotris(phosphonio) borat-Typ**", Angewandte Chemie, vol. 100, No. 8, p. 1135-1138, 1988}.*

Mueller et al., {Bis[boranatobis(dimethylphosphoniumylidenemethylide)] complexes of manganese(II) and cobalt(II): stable, homoleptic tetraalkyls of paramagnetic transition-metal centers, Organometallics (1983), 2(2), 257-63}.*

Yoshikazu Yamamoto et al., "Facile Synthesis of Highly Congested 1, 2-Diphosphinobenzenes from Bis(phosphine) boronium Salts", Organic Letters, vol. 8, No. 26, p. 6103-6106, Published on Web Nov. 23, 2006, American Chemical Society.

Yasuro Kawano et al., "BH Bond Activation of Trimethylphosphineborane by Transition Metal Complexes: Synthesis of Metal Complexes Bearing Nonsubstituted Boryl—Trimethylphosphine, Cp*M(CO)3(BH2.PMe3) (M=Mo, W)", Journal of the American Chemical Society, vol. 121, No. 50, p. 11744-11750, Published on Web Dec. 4, 1999.

A. Ba-Isa et al., "Desorption Ionization Mass Spectrometry, Secondary Ion Mass Spectra of Phosphonium Salts", Tetrahedron, vol. 39, No. 4, p. 591-597, 1982.

Von Hubert Schmidbaur et al., "Dikationen vom Hydrotris(phosphonio) borat-Typ**", Angewandte Chemie, vol. 100, No. 8, p. 1135-1138, 1988.

* cited by examiner

*Primary Examiner*—Sikarl A Witherspoon
*Assistant Examiner*—Chukwuma O Nwaonicha
(74) *Attorney, Agent, or Firm*—Marvin Motsenbocker; Mots Law, PLLC

(57) ABSTRACT

The present invention aims to provide a bis(phosphine) boronium salt to be used as a building block or the like for producing a diphosphine compound effective mainly for various kinds of transition metal-catalyzed reactions and further to provide a preferable production method of the bis(phosphine) boronium salt and a bis(phosphine) boronium salt to be produced by the production method.

The present invention provides a bis(phosphine) boronium salt having the structure defined by the following formula (1).

(1)

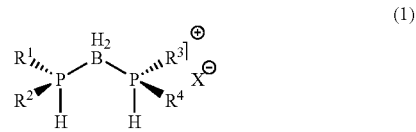

7 Claims, 1 Drawing Sheet

BIS(PHOSPHINE) BORONIUM SALT, PRODUCTION METHOD OF BIS(PHOSPHINE) BORONIUM SALT, AND BIS(PHOSPHINE) BORONIUM SALT PRODUCED BY THE PRODUCTION METHOD

TECHNICAL FIELD

The present invention relates to a bis(phosphine) boronium salt to be used as a building block or the like for producing a diphosphine compound effective mainly for various transition metal-catalyzed reactions, a production method of a bis (phosphine) boronium salt, and a bis(phosphine) boronium salt produced by the production method.

BACKGROUND ART

It is reported that a phosphine ligand having a sterically complicated structure is useful for various transition metal-catalyzed reactions such as cross-coupling and investigations on synthesis of phosphine compounds have been addressed as a most important issue at home and abroad (for example, Patent Documents 1 to 3) and have drawn attention as an important approach to develop a highly practical catalytic organic transformation process.

Patent Document 1: JP 2001-253889 A
Patent Document 2: JP 2003-292498 A
Patent Document 3: JP 2003-313194 A

DISCLOSURE OF THE INVENTION

Problems to be Solved by the Invention

However, with respect to synthesis of a diphosphine compound having two phosphino groups at close positions (particularly neighboring positions) and a further sterically complicated structure, almost no effective synthesis process has been proposed so far.

The reason for that is attributed to the complicated steric structure of the diphosphine compound: that is, if two phosphino groups are introduced step by step into close positions, steric hindrance is caused in the introduction of the phosphino group in the second stage and accordingly the reaction is considerably inhibited.

Therefore, the present inventors have made intensive investigations to solve such a problem and consequently have developed a bis(phosphine) boronium salt having a structure comprising two phosphino groups bonded by boronium crosslinking, and have found that if a bis(phosphine) boronium salt is used as a building block for producing a diphosphine compound, the phosphine introduction reaction in the second stage becomes an inter-molecular reaction and the reaction can be relatively smoothly promoted.

Further, the present inventors have also found that the boronium crosslinking portion in the intermediate product after the coupling reaction also works as a protection group for the phosphino group which is relatively easily oxidized, and can be removed easily by a simple operation.

Further, the present inventors have also found that it is possible to easily obtain diphosphine compounds in various structures by combining bis(phosphine) boronium salts in various structures with electrophilic agents.

The present invention has been accomplished based on the above-mentioned findings and aims to provide a bis(phosphine) boronium salt to be used as a building block or the like for producing a diphosphine compound effective for various transition metal-catalyzed reactions as well as a preferable production method of such bis(phosphine) boronium salt and a bis(phosphine) boronium salt produced by the production method.

Means for Solving the Problems

The bis(phosphine) boronium salt of the present invention is a compound having the structure defined by the following formula (1):

[Chem. 2]

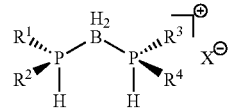

(1)

that is, a compound having a structure in which two phosphino groups are crosslinked by the boronium portion and is useful as a building block or the like for producing a diphosphine compound effective mainly for various transition metal-catalyzed reactions.

The diphosphine compound to be produced using the bis (phosphine) boronium salt of the present invention as a building block may be a compound having the structure defined by the following formula (2):

[Chem. 3]

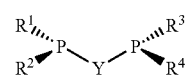

(2)

that is, a compound having a structure comprising two phosphino groups introduced into a backbone portion Y.

That is, in the case two phosphino groups are to be introduced into a certain backbone portion in a nucleophilic manner, if phosphineborane or phosphine oxide having large substituent groups as a nucleophilic agent, significant steric hindrance is caused to make promotion of the reaction difficult and particularly, in the case of introducing an alkyl-substituted bulky phosphino group such as dialkylphosphine, the reaction is not at all promoted and the synthesis is regarded to be extremely difficult.

In this respect, if the bis(phosphine) boronium salt of the present invention is used as a building block for synthesizing a diphosphine compound, the problem of steric hindrance can be avoided and therefore, synthesis of a large amount of diphosphine, which has been conventionally impossible to be carried out, can be accomplished.

The synthesis of a diphosphine compound using the bis (phosphine) boronium salt of the present invention as a building block involves synthesizing, preferably under a basic condition, an intermediate product by a coupling reaction of the bis(phosphine) boronium salt of the present invention and an electrophilic agent having at least two electrophilic portions and then subjecting the intermediate product to treatment with a de-boronium agent (see the following formula (3)).

[Chem. 4]

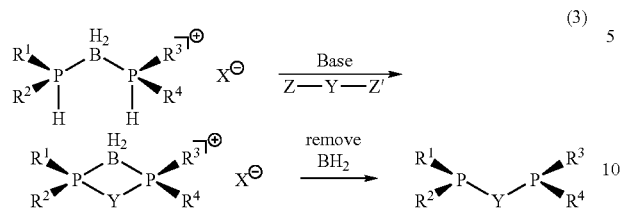
(3)

That is, since two phosphorus atoms exist as nucleophilic portions in the bis(phosphine) boronium salt of the present invention, the coupling reaction with the electrophilic agent having at least two electrophilic portions is relatively smoothly promoted and after the coupling of one phosphorus atom with one electrophilic portion is accomplished, the other coupling (in the second step) becomes an inter-molecular reaction and thus inhibition of the reaction due to the steric hindrance can be avoided.

Further, the structures and types of substituent groups on two phosphorus atoms in the diphosphine compound to be produced are determined according to the structures and types of the substituent groups on two phosphorus atoms in the bis(phosphine) boronium salt of the present invention and therefore, it is made possible to produce diphosphine compounds having various steric and electronic properties by properly selecting the structures of the substituent groups on these two phosphorus atoms in the bis(phosphine) boronium salt of the present invention.

In addition, the backbone portion Y of the diphosphine compound to be produced is determined according to the structure of the electrophilic agent having at least two electrophilic portions and therefore, it is made possible to produce diphosphine compounds having various backbone portions by properly selecting the electrophilic agent.

The types and structures of the counter ion [X−] in the bis(phosphine) boronium salt of the present invention are not particularly limited and various kinds of anions may be properly selected, and specifically halogens such as $F^-$, $Cl^-$, $Br^-$, and $I^-$, and $CF_3SO_3^-$, $BF_4^-$, $PF_6^-$, and $SbF_6^-$ are generally used.

Herein, a synthetic method of the bis(phosphine) boronium salt of the present invention is not particularly limited, however the present inventors have found a production method of the bis(phosphine) boronium salt of the present invention described below as a preferable synthetic method of the salt.

Hereinafter, the production method of the bis(phosphine) boronium salt of the present invention which can preferably synthesize the bis(phosphine) boronium salt of the present invention (hereinafter, referred to as the method of the present invention) will be described in detail.

The method of the present invention has roughly two synthesis routes: a symmetric synthesis route and an asymmetric synthesis route.

The former symmetric synthesis route is the simplest production method of the bis(phosphine) boronium salt and characterized in that a phosphine compound is treated with mono-substituted borane (see the following reaction formula (4)).

[Chem. 5]

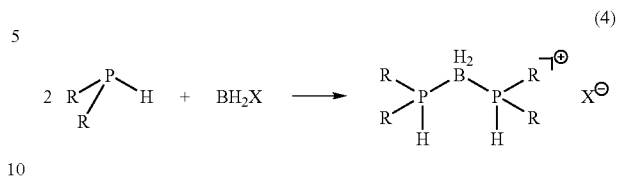
(4)

That is, the above-mentioned symmetric synthesis route involves treatment of various kinds of phosphine compounds having desired substituent groups such as phosphine, monoalkylphosphine, dialkylphosphine, monoarylphosphine, diarylphosphine, or alkylarylpyhosphine with 0.5 equivalent of mono-substituted borane of which hydrogen group on the boron atom is mono-substituted with a halogen or trifluoromethanesulfonyloxy group, and use of the phosphine compound having various steric and electronic characteristics gives various kinds of symmetric bis(phosphine) boronium salts.

However, in this symmetric synthesis route, asymmetric bis(phosphine) boronium salts having different substitution patterns on two phosphorus atoms cannot be produced.

Herein, in the case of synthesizing an asymmetric bis(phosphine) boronium salt having different substitution patterns on two phosphorus atoms, the simplest solving means may be a means of adding two types of phosphine compounds in one equivalent each to the mono-substituted borane step by step, however the present inventors have found the latter asymmetric synthesis route to more clearly carry out the reaction.

That is, the asymmetric synthesis route is characterized in that phosphine compounds are treated with phosphineborane of which hydrogen group on the boron atom is mono-substituted (see the following reaction formula (5)), and more particularly, phosphine compounds are treated with phosphineborane of which hydrogen group on the borane atom is mono-substituted with a halogen or trifluoromethanesulfonyloxy group.

[Chem. 6]

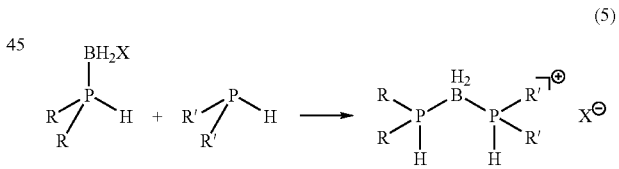
(5)

Herein, as $R^1$, $R^2$, $R^3$, and $R^4$, which are substituent groups on the phosphorus atom in the bis(phosphine) boronium salt of the present invention, an alkyl group, an aryl group, a hydroxyl group, an alkoxy group or other substituent groups of desired types or structures may be properly selected without any limitation, however, an alkyl group, an aryl group, and an alkoxy group are generally preferably selected Practically, the above-mentioned alkyl group may be selected properly from a methyl group, an ethyl group, an isopropyl group, a cyclohexyl group, a tert-butyl group, an adamantyl group, a benzyl group and the like in order to variously change the steric properties of the diphosphine to be obtained finally.

In consideration of the effect of electrons in addition to the steric properties, the above-mentioned aryl group may be selected properly from a phenyl group, an o-tolyl group, an m-tolyl group, a p-tolyl group, a 3,5-xylyl group, a 3,5-diisopropylphenyl group, a p-anisyl group, a p-trifluoromethylphenyl group, an α-naphthyl group, a β-naphthyl group and the like, and the alkoxy group may be selected properly from a methoxy group, an ethoxy group, an isopropoxy group, a tert-butoxy group, a phenoxy group and the like.

Since it is confirmed that high reactivity and stereoselectivity can be obtained in rhodium-catalyzed asymmetric hydrogenation or a palladium-catalyzed asymmetric carbon-carbon bond formation reaction using P-chiral phosphines having the asymmetric center on the phosphorus atom, it is preferable for the diphosphine compound produced using the bis(phosphine) boronium salt of the present invention as a building block that the phosphorus atom forms the asymmetric center.

In this respect, by using a compound containing a phosphorus atom forming the asymmetric center as a phosphine compound, a starting material, the method of the present invention makes it possible to produce a bis(phosphine) boronium salt having the asymmetric center on at least one of phosphorus atoms and use of the bis(phosphine) boronium salt as a building block makes it possible to produce a diphosphine compound having the asymmetric center on the phosphorus atom.

Further, in coupling reactions using various kinds of transition metal catalysts having monophosphine as a ligand, it is supposed that the reaction is smoothly promoted owing to prevention of stable dimer formation during the reaction by the catalytic active species because of the bulky ligand, that is, the steric hindrance, and accordingly, also with respect to the diphosphine compound to be produced using the bis(phosphine) boronium salt of the present invention as a building block, it is preferable to select a substituent group having a bulky structure for at least one of substituent groups $R^1$ to $R^4$, for example, an alkyl group having a branched structure such as a tert-butyl group; an alkyl group having a cyclic structure such as a cyclohexyl group and an adamantyl group; and an aryl group.

In this respect, in the method of the present invention, it is made possible to produce a bis(phosphine) boronium salt having a bulky structure for at least one of the substituent groups $R^1$ to $R^4$ on the phosphorus atom by selecting a compound having a substituent group with a bulky structure, for example, an alkyl group having a branched structure such as a tert-butyl group; an alkyl group having a cyclic structure such as an adamantyl group and a cyclohexyl group; and an aryl group, for at least one of substituent groups on the phosphorus atom of the phosphine compound as a starting material, and by using the bis(phosphine) boronium salt as a building block, the diphosphine compound having a bulky structure for at least one of substituent groups of the phosphorus atom can be produced.

Use of the bis(phosphine) boronium salt of the present invention produced by the production method of the present invention mainly as a building block for synthesizing a diphosphine compound makes it possible to avoid the problem of the steric hindrance and to accomplish synthesis of a large amount of diphosphine which could not be conventionally synthesized.

EFFECTS OF THE INVENTION

The bis(phosphine) boronium salt of the present invention has the above-mentioned structure and is a novel compound capable of giving diphosphine compounds having various structures by a simple synthetic process.

That is, if the bis(phosphine) boronium salt of the present invention is used as a building block for producing a diphosphine compound, the phosphine introduction reaction in the second stage becomes the intramolecular reaction and is relatively smoothly promoted.

The boronium crosslinking portion in an intermediate product after the coupling reaction works as a protection group for the phosphino groups, which tend to be oxidized relatively easily, and further it is easy to remove the portion by treatment with various kinds of de-boronium agents such as fluoride anions.

Further, combination of the bis(phosphine) boronium salt of the present invention which has various structures with an electrophilic agent can easily give diphosphine compounds having various structures.

The method of the present invention is a method preferable for producing the above-mentioned bis(phosphine) boronium salt of the present invention and includes two synthesis routes: a symmetric synthesis route and an asymmetric synthetic route.

The former symmetric synthetic route is characterized in that a phosphine compound is treated with mono-substituted borane having a substituent group for a hydrogen group on the boron atom and use of phosphine compounds having various steric and electronic characteristics makes it possible to give various kinds of symmetric bis(phosphine) boronium salts.

On the other hand, the latter asymmetric synthetic route is characterized in that phosphine compounds are treated with phosphineborane of which hydrogen group on the boron atom is mono-substituted, and it is possible to synthesize asymmetric bis(phosphine) boronium salts having various substitution patterns on two phosphorus atoms.

Accordingly, if the bis(phosphine) boronium salt of the present invention produced by the method of the present invention is used mainly as a building block for synthesizing a diphosphine compound, the problem of steric hindrance can be avoided and therefore, synthesis of a large amount of diphosphine, which has been conventionally impossible to be carried out, can be accomplished.

EXPLANATION OF SYMBOLS

1 deprotonated bis(phosphine)boronium salt
2 diphosphine compound
3 electrophilic agent
4 intermediate product
5 deprotonated phosphineborane

BEST MODES FOR CARRYING OUT THE INVENTION

Hereinafter, Examples of the present invention will be described, however it is not intended that the present invention be limited to the described Examples.

Figure 1:
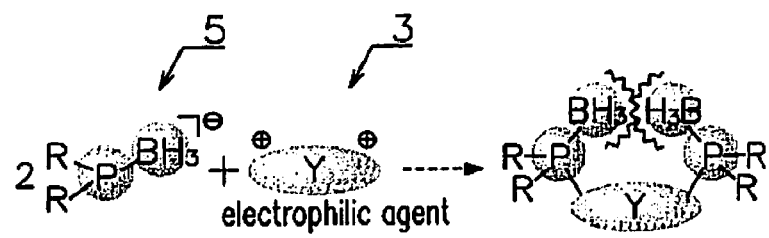
FIG. 1 is a schematic view showing a state of introducing two phosphino groups into a certain backbone portion in a nucleophilic manner using phosphineborane.

FIG. 1 illustrates a conventional method for introducing two phosphino groups into an electrophilic agent 3 having a certain backbone portion in a nucleophilic manner using phosphineborane (deprotonated form) 5: that is, if the phosphineborane 5 is used as a nucleophilic agent, significant steric hindrance is caused at the time of introduction of the phosphino group in the second stage and accordingly the reaction is hardly promoted and particularly, the reaction of introduction of an alkyl-substituted bulky phosphino group such as dialkylphosphine cannot be promoted at all.

Figure 2:
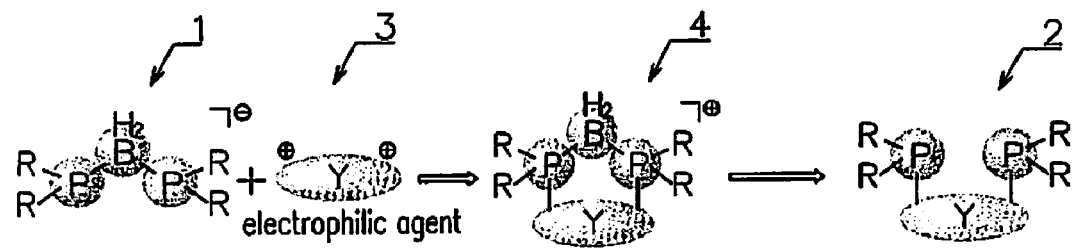
FIG. 2 is a schematic view showing a state of introducing two phosphino groups into a certain backbone portion in a nucleophilic manner using a bis(phosphine)boronium salt of the present invention.

On the other hand, FIG. 2 illustrates a method for introducing two phosphino groups into an electrophilic agent 3 having a certain backbone portion in a nucleophilic manner using a bis(phosphine) boronium salt (deprotonated form) 1 of the present invention: that is, since the bis(phosphine) boronium salt 1 of the present invention is used as a building block for the synthesis of a diphosphine compound 2, the phosphine introduction reaction in the second stage becomes an intramolecular reaction to avoid the problem of the steric hindrance and therefore, synthesis of a large amount of diphosphine compounds 2, which cannot be conventionally synthesized, can be accomplished.

Table 1 shows examples of various kinds of structures of diphosphine compounds produced by a coupling reaction of the bis(phosphine) boronium salt of the present invention with electrophilic agents having various structures.

TABLE 1

| Electrophilic agent | Bis(phosphine) boronium salt | Intermediate product | Diphosphine compound |
|---|---|---|---|

TABLE 1-continued

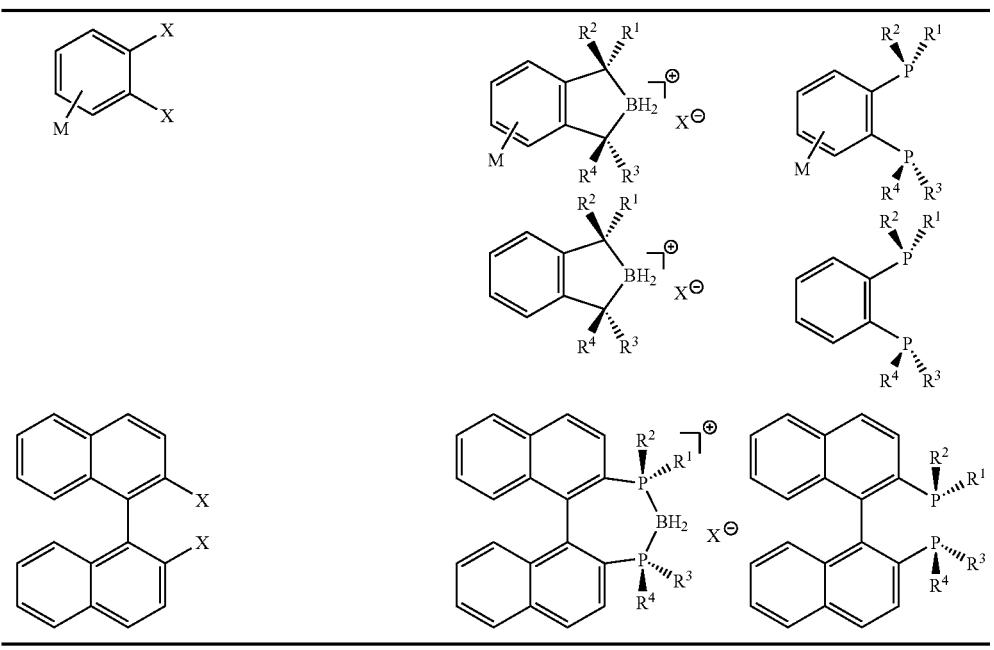

That is, combinations of the bis(phosphine) boronium salt of the present invention with electrophilic agents having various structures easily gives diphosphine compounds in various structures and a library of diphosphine compounds can be built according to the combinations.

Example 1

Preparation of (S)-(tert-butyl(methyl)phosphine)(di-tert-butylphosphine) boronium iodide A 30 mL two-necked eggplant flask was charged with 133 mg of lithium aluminum hydride and a magnetic stirrer and purged with nitrogen and 5 mL of diethyl ether was added and the contents were cooled to 0° C. while being stirred.

Further, 627 µL of di-tert-butylchlorophosphine was added and after the resulting mixture was stirred at room temperature for 1 hour, the resulting reaction solution was filtered by passing the solution through about 3 mg of basic alumina under nitrogen gas flow and eluted with about 15 mL of diethyl ether.

The filtrate was concentrated under reduced pressure and the obtained residue was dissolved in 9 mL of dichloromethane after reintroduction of nitrogen.

Meanwhile, a 30 mL two-necked eggplant flask was charged with 300 mg of (S)-tert-butyl(methyl)phosphineborane, 323 mg of iodine, and a magnetic stirrer and purged with nitrogen and 5 mL of dichloromethane was added for dissolution and the resulting solution was stirred at room temperature for 7 hours and mixed with the prepared dichloromethane solution of di-tert-butylphosphine at room temperature and stirred for 24 hours.

After 1 mL of a 1.2 M borane-tetrahydrofuran complex tetrahydrofuran solution was added and stirred at room temperature for 30 minutes, 5 mL of water and 7 mL of dichloromethane were added and after the resulting mixture was fiercely stirred and an organic layer and a water layer were separated, the water layer was extracted with 7 mL of dichloromethane two times and sodium sulfate was added to dehydrate the organic layer.

The resulting product was filtered and the filtrate was concentrated by a rotary evaporator to obtain a residue which was purified by silica gel column chromatography (chloroform/methanol=20/1→10/1) to obtain 618 mg of (S)-(tert-butyl (methyl)phosphine)(di-tert-butylphosphine) boronium iodide as a white solid (yield 62%).

Example 2

Preparation of bis(di-tert-butylphosphine)boronium bromide

A 30 mL two-necked eggplant flask was charged with 229 mg of lithium aluminum hydride and a magnetic stirrer and purged with nitrogen and 5 mL of diethyl ether was added and the contents were cooled to 0° C. while being stirred.

Further, 1.08 mL of di-tert-butylchlorophosphine was added and stirred at room temperature for 1 hour, and thereafter, the resulting reaction solution was filtered by passing the solution through about 3 g of basic alumina under nitrogen gas flow and eluted with about 15 mL of diethyl ether.

The filtrate was concentrated under reduced pressure and after nitrogen reintroduction, the obtained residue was dissolved in 10 mL of dichloromethane and mixed with 2.7 mL of a 1.0 M monobromoborane-methyl sulfide complex dichloromethane solution at room temperature and stirred for 40 hours.

The resulting reaction solution was concentrated under reduced pressure and the obtained residue was purified by silica gel column chromatography (chloroform/methanol=20/1→10/1) to obtain 743 mg of bis(di-tert-butylphosphine)boronium bromide as a white solid (yield 72%).

Example 3

Preparation of meso- and (S,S)-bis(tert-butyl(methyl)phosphine)boronium iodide A 50 mL two-necked eggplant flask was charged with 3.04 g of potassium carbonate, 1.02 g of tert-butyl(methyl)phosphonium iodide, and a magnetic stirrer and purged with nitrogen and 10 mL of dichloromethane was added.

After the contents were stirred at room temperature for 1 hour, the resulting reaction solution was filtered by passing the solution through about 3 g of basic alumina under nitrogen gas flow and eluted with about 15 mL of dichloromethane.

Meanwhile, a 100 mL two-mouth eggplant flask was loaded with 400 mg of (S)-tert-butyl(methyl)phosphineborane, 430 mg of iodine, and a magnetic stirrer and purged with nitrogen and 5 mL of dichloromethane was added for dissolution and the resulting solution was stirred at room temperature for 7 hours and mixed with the prepared tert-butyl(methyl)phosphine dichloromethane solution at room temperature and stirred for 24 hours.

After 1.4 mL of a 1.2 M borane-tetrahydrofuran complex tetrahydrofuran solution was added and stirred at room temperature for 30 minutes, 5 mL of water and 7 mL of dichloromethane were added and after the resulting mixture was fiercely stirred and an organic layer and a water layer were separated, the water layer was extracted with 7 mL of dichloromethane two times and sodium sulfate was added to dehydrate the organic layer.

The resulting product was filtered and the filtrate was concentrated by a rotary evaporator to obtain a residue which was refined by silica gel column chromatography (chloroform/methanol=20/1→10/1) to obtain 697 mg of bis(tert-butyl(methyl)phosphine)boronium iodide as a mixture of meso and (S,S) isomers as a white solid (yield 59%).

The obtained product was dissolved in 6 mL of tetrahydrofuran and recrystallized to obtain 208 mg of meso isomer as a plate-like crystal and 151 mg of (S,S) isomer as a needle-like crystal.

Example 4

Preparation of bis(diphenylphosphine)boronium bromide

A 30 mL two-necked eggplant flask was charged with 20 mL of a hexane solution containing 10% by weight of diphenylphosphine and a magnetic stirrer and the solution was concentrated under reduced pressure and after nitrogen introduction, the obtained residue was dissolved in 5 mL of dichloromethane.

Further, 3.5 mL of a 1.0 M monobromoborane-methyl sulfide complex dichloromethane solution was added to the resulting solution at room temperature and stirred for 35 hours.

Further, the resulting reaction solution was concentrated under reduced pressure and the obtained residue was washed with tetrahydrofuran to obtain 1.0 g of bis(diphenylphosphine)boronium bromide as a white solid (yield 65%).

What is claimed is:

1. A bis(phosphine) boronium salt having the structure defined by the following formula:

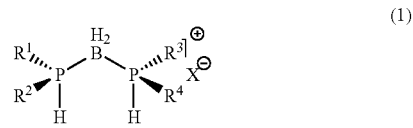

(1)

wherein R1, R2, R3, and R4 are independently selected from the group consisting of an alkyl group, an aryl group, a hydroxyl group, and an alkoxy group, and wherein X is selected from the group consisting of a halide ion, $CF_3SO_3-$, $BF_4-$, $PF_6-$ and $SbF_6-$.

2. A production method of the bis(phosphine) boronium salt according to claim 1, comprising treatment of a phosphine compound with mono-substituted borane.

3. A production method of the bis(phosphine) boronium salt according to claim 1, comprising treatment of a phosphine compound with mono-substituted phosphineborane having a substituent group for a hydrogen atom on the boron atom.

4. The production method of the bis(phosphine) boronium salt according to claim 2, wherein the phosphorus atom of the phosphine compound forms an asymmetric center.

5. The production method of the bis(phosphine) boronium salt according to claim 2, wherein at least one of substituent groups of the phosphine compound is an alkyl group having a branched structure, an alkyl group having a cyclic structure, or an aryl group.

6. A bis(phosphine) boronium salt produced by the production method of a bis(phosphine) boronium salt according to claim 2.

7. A bis(phosphine) boronium salt as described in claim 1, wherein the alkyl group is selected from the group consisting of a methyl group, an ethyl group, an isopropyl group, a cyclohexyl group, a tert-butyl group, an adamantyl group and a benzyl group.

* * * * *